US011664102B2

(12) United States Patent
DeCiccio et al.

(10) Patent No.: US 11,664,102 B2
(45) Date of Patent: May 30, 2023

(54) PHARMACY FULFILLMENT AND VERIFICATION OF NON-STERILE COMPOUNDING

(71) Applicant: Vitae Industries, Inc., Providence, RI (US)

(72) Inventors: Daniel John DeCiccio, Winter Park, FL (US); Jeanine Sinanan-Singh, Orlando, FL (US)

(73) Assignee: VITAE INDUSTRIES, Providence, RI (US)

( * ) Notice: Subject to any disclaimer, the term of this patent is extended or adjusted under 35 U.S.C. 154(b) by 0 days.

(21) Appl. No.: 16/034,090

(22) Filed: Jul. 12, 2018

(65) Prior Publication Data

US 2019/0019576 A1 Jan. 17, 2019

Related U.S. Application Data

(60) Provisional application No. 62/531,862, filed on Jul. 12, 2017.

(51) Int. Cl.
*G16H 20/13* (2018.01)
*B65B 3/00* (2006.01)
(Continued)

(52) U.S. Cl.
CPC ............ *G16H 20/13* (2018.01); *B65B 3/003* (2013.01); *B65B 9/045* (2013.01); *B65B 61/26* (2013.01);
(Continued)

(58) Field of Classification Search
CPC ........ G16H 20/13; G16H 20/17; G16H 40/20; G16H 10/60; B65B 31/02; B65B 31/024; B65B 3/003; A61J 3/002
(Continued)

(56) References Cited

U.S. PATENT DOCUMENTS

| 2004/0005182 A1* | 1/2004 | Gaylo ..................... B29C 41/46 400/283 |
| 2007/0088567 A1* | 4/2007 | Berkelhamer ......... G06Q 50/24 705/2 |
| 2007/0255595 A1* | 11/2007 | Nickell .................. G16H 20/13 705/2 |

FOREIGN PATENT DOCUMENTS

| WO | WO-2004005014 A2 * | 1/2004 | ............ B22F 3/1055 |
| WO | WO-2016038356 A1 * | 3/2016 | ........... A61K 9/0087 |

OTHER PUBLICATIONS

Model Standards for Pharmacy Compounding of Non-Sterile Preparation; Draft 5b Non-Sterile Preparations Aug. 5, 2016, National Association of Pharmacy Regulatory Authorities (Year: 2016).*

(Continued)

*Primary Examiner* — Hiep V Nguyen

(57) ABSTRACT

A method and apparatus for pharmacy fulfillment and verification of non-sterile compounding. A system includes an entry node, the entry node including at least a processor, a memory and an input/output device, the memory including at least an operating system and an order entry process, and a pharmacy fulfillment and verification of non-sterile compounding system, the entry node communicatively linked to the pharmacy fulfillment and verification of non-sterile compounding system, the pharmacy fulfillment and verification of non-sterile compounding system including a set of components, the set of components including at least a formulating component, a fabrication component and a dispensing component.

20 Claims, 2 Drawing Sheets

(51) Int. Cl.
*G16H 10/60* (2018.01)
*G16H 40/20* (2018.01)
*B65B 61/26* (2006.01)
*B65B 9/04* (2006.01)
*A61J 3/00* (2006.01)

(52) U.S. Cl.
CPC ............ *G16H 10/60* (2018.01); *G16H 40/20* (2018.01); *A61J 3/002* (2013.01)

(58) Field of Classification Search
USPC .......................................................... 705/2
See application file for complete search history.

(56) References Cited

OTHER PUBLICATIONS

Drug Distribution and Control: Preparation and Handling—Technical Assistance Bulletin, American Society of Hospital Pharmacists. ASHP technical assistance bulletin on compounding nonsterile products in pharmacies. Am J Hosp Pharm. 1994; 51:1441-8 (Year: 1994).*

Rodney W. Hicks; The importance of correct compounding practices; Feb. 2015 vol. 101 No. 2 • Periop Briefing (Year: 2015).*

* cited by examiner

900

Receiving and entering a prescription
1000
|
V
Compound identification and batching
2000
|
V
Compound formulation
3000
|
V
Compound preparation
4000
|
V
Compound/prescription verification
5000
|
V
Final notification
6000

FIG. 2

PHARMACY FULFILLMENT AND VERIFICATION OF NON-STERILE COMPOUNDING

CROSS REFERENCE TO RELATED APPLICATIONS

This application claims benefit from U.S. Provisional Patent Application Ser. No. 62/531,862, filed Jul. 12, 2017, which is incorporated by reference in its entirety.

STATEMENT REGARDING GOVERNMENT INTEREST

None.

BACKGROUND OF THE INVENTION

The present invention relates generally to compounding, and more particularly to pharmacy fulfillment and verification of non-sterile compounding.

Compounding is the millennia-old practice of preparing patient-specific medication doses. Compounding pharmaceuticals generally includes combining one or more active or therapeutic ingredients with one or more carrier substances or mediums. The compounding process must be done for medically necessary reasons, such as to change the form of the medication from a solid pill to a liquid, to avoid a non-essential ingredient that the patient is allergic to, or to obtain the exact dose needed as medically necessary. The compounding process may also be done for voluntary reasons to address issues including pediatric adherence to prescription medications, such as adding favorite flavors to a medication.

The operational and performance demands upon these compounding systems and methodologies are becoming increasingly more complex and sophisticated, in terms of, for example, safety, speed, reliability, accuracy, overall user friendliness and ergonomics, and so forth. The operational and performance demands upon these compounding systems and methodologies are also becoming increasingly more complex and sophisticated with regard to the management of patient and prescription information, in terms of providing an information path that starts with the clinician and finishes with the final product delivery to the end patient.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features a method including receiving a prescription for a non-sterile compound from a health care provider, identifying the non-sterile compound, batching the non-sterile compound for a compounding process, and formulating the identified non-sterile compound.

In another aspect, the invention features a system including an entry node, the entry node including at least a processor, a memory and an input/output device, the memory including at least an operating system and an order entry process, and a pharmacy fulfillment and verification of non-sterile compounding system, the entry node communicatively linked to the pharmacy fulfillment and verification of non-sterile compounding system, the pharmacy fulfillment and verification of non-sterile compounding system including a set of components, the set of components including at least a formulating component, a fabrication component and a dispensing component.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

FIG. 2 is a flow diagram.

DETAILED DESCRIPTION

Figure 1:
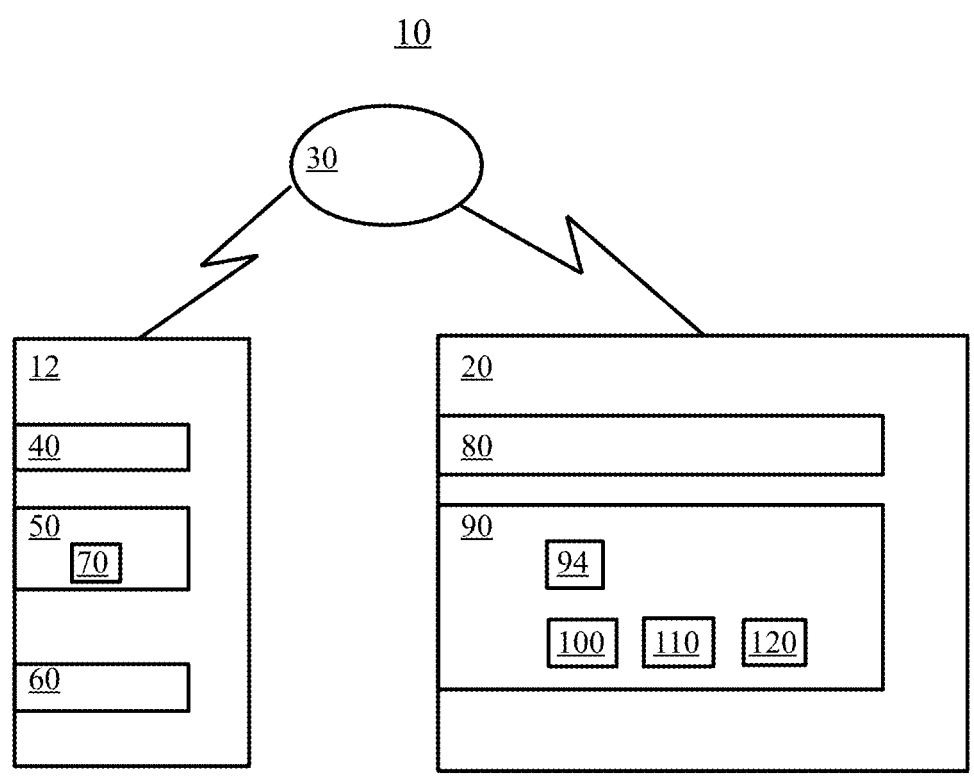
FIG. 1 is a block diagram of an exemplary pharmacy fulfillment and verification of non-sterile compounding system.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

Pharmaceutical compounding is the preparation of personalized medications in response to an individual patient prescription by a licensed pharmacist or physician. Current processes are inefficient and error-prone due to manual, labor-intensive preparation methods. Moreover, non-sterile compounding is largely unautomated. Some non-sterile dosage forms, such as gummies, can take an hour to prepare using current methods.

Current manual methods, including capsule filling devices, limit efficient batching. In general, batching prescriptions requires the same active ingredient, same strength and same dosage form. This restricts the efficiency of non-sterile compounding workflows.

Every batch is subject to varying errors, including human errors, at every step. Final dosage forms are inconsistent within the pharmacy and across different pharmacies. The Food and Drug Administration (FDA) found that the actual dose of compounded oral medications ranged from 67.5% to 268.4% of the dose on the label. Together, inefficient batching and manual preparation methods create waste. Pharmacies often add 10% or other fixed amount extra in formulas to account for inevitable waste/loss in the preparation process. This fixed amount is not empirically derived.

Limited verification procedures exacerbate the consistency and accuracy issue. Individual compounding pharmacies may institute processes that mandate validating dose by weighing a sample from each batch. However, it is rarely required. More importantly, transparency and consistent quality measure recording are limited. Aggregate data about compounded drugs is largely inaccessible. Many do not initiate insurance claims. Product data is locked up in thousands of independent pharmacies.

Many patients need personalized medications, but the inefficiency of compounding limits their accessibility. Compounded liquid formulations are more prevalent because they are much easier to make than any solid oral dosage form. However, liquid formulations present many problems from measuring errors and dosing issues to storage and transportation costs. The World Health Organization (WHO) recommends "flexible solid oral dosage forms" for children worldwide. Children and other populations, including the elderly, require a range of lower doses that are not commercially available. Efficient, cost-effective compounding of solid dosage forms is essential to serving these populations.

Current compounding processes add significant friction to current efficient pharmacy workflows. Pharmacies either omit compounding or work around the disruption, often by separating compounding work. In addition to interrupting existing pharmacy workflows, compounding requires specialized skills to effectively execute these manual procedures. Overall, methods and processes for preparing personalized medications can be optimized and improved with automation and less disruptive integration into pharmacy workflows.

Pharmacy dispensing and fulfillment is moving toward greater automation. The present invention focuses on pharmacy compounding that can be completely automated. Partial and complete pharmacy automation require workflows disclosed herein. Traditional processes and procedures change and are not simply mimicking and replacing current human activities. Increased automation in compounding preparation further increases efficiency by disrupting major workflow processes including batching and verification. Finer control over the final dosage form including shape and size adds new considerations to the compounding process. In addition, bringing the preparation process "online" enables unprecedented visibility into data about customized medications. Currently, there is little to no visibility into what raw APIs are used, doses and dosage forms created as compounded prescriptions because often there are no insurance claims or specific orders from wholesalers/manufacturers to aggregate.

In FIG. 1, an exemplary system 10 includes a pharmacy node 12 communicatively linked to an automated modular compound fulfillment system 20. Although only one pharmacy node 12 is shown, the system 10 may include one or more additional pharmacy nodes communicatively linked to the automated modular compound fulfillment system 20.

The link between the pharmacy node 12 and the automated modular compound fulfillment system 20 may be wired or wireless. In implementations, communication between the pharmacy node 12 and the automated modular compound fulfillment system 20 may be provided by a network 30 of interconnected computers (e.g., the Internet), a wide area network (WAN), a local area network (LAN), a virtual private network (VPN), or combinations thereof.

The pharmacy node 12 includes at least a processor 40, a memory 50 and an input/output device 60, such as a display, keyboard and/or mouse. The memory 50 includes at least an operating system and an order entry process 70.

The automated modular compound fulfillment system 20 includes at least a processor 80 and a memory 90 having at least an operating system 94 and one or more components, such as a formulating component 100, a fabrication component 110 and a dispensing component 120.

The formulating component 100 receives prescription data from the order entry process 70 and extracts dosage form, drug, strength, quantity, patient allergies, reason for compounding, urgency, patient address, delivery or pick-up request, and generates a work order. The formulating component 100 may generate and transmit secure message/request to prompt the responsible physician for information for fields that are unclear, nonsensical or invalid, and/or to approve changes (when required by law), such as changing pharmacy.

The fabrication component 110 reads work order received from the formulating component 100, computes appropriate motor instructions for an automated compounding machine to extrude a correct amount per a dosage based on API/formulation and strength. Additional instructions may be generated to adjust heaters and/or fans to warm and/or cool build surfaces, and/or parts of the cartridge based on the formulation introduced and dosage form requested. A departure from the normal process involving human massing for QC, the system may turn on a camera for verification purposes. In addition, this automated system operates on liquid phase formulations in cases when the compounding pharmacy would normally be working with solids (e.g. powders to make capsules or tablets). Thus, the system must also generate instructions and operate cameras and/or other sensors to ensure the cartridge and formulation achieves the appropriate state (e.g., "tip" primed with the fluid to avoid "dry" runs at the start) before beginning production. It then executes computed instructions to produce final dosage forms to fulfill order.

The dispensing component 120 receives final dosage forms from the fabrication component 110 packages and labels the order for dispensing to the patient.

In summary, a physician writes a compound prescription and it is entered into the automated modular compound fulfillment system 20, which verifies it, schedules it, produces it, packages it and dispenses it. The automated modular compound fulfillment system 20 enables real-time compounding fulfillment.

As shown in FIG. 2, an exemplary pharmacy fulfillment and verification of non-sterile compounding process 900 includes receiving and entering (1000) a prescription.

The pharmacy fulfillment and verification of non-sterile compounding process 900 includes compound identification and batching (2000).

Compound identification and batching (2000) includes the use of ingredients/materials and allocation of resources/time. A computer program accesses pharmacy prescriptions and identifies prescriptions that require compounding. These prescriptions are then grouped by dosage form (e.g. capsule, tablet, etc.) and active ingredient (drug). Compound identification and batching (2000) cross-references available resources including compounding equipment, personnel and training level to determine preparation method for each dosage form. Prescriptions, especially solid dosage forms that can be prepared using available automated compounding equipment, are identified and proceed to efficient batching process. Normally, prescriptions are batched by dosage form, active ingredient and strength (dose). In this process, dosage forms are prepared using dose-agnostic methods. Thus, they can be batched by dosage form and active ingredient. Priority-ordered prescriptions provided to batching routine are grouped to optimize preparation speed, use of ingredients (minimize waste) and final dosage form size.

For example, consider five prescriptions for the same drug each with a different strength. Strengths range between 10 mg and 200 mg. All five prescriptions could be made using one stock formula with a fixed concentration. However, the final dosage form for the highest strength prescription would be 20 times larger than the smallest, which may break accepted tablet maximum sizes. In addition, a fixed concentration could result in greater waste of materials, as leftover formula may not be easily saved for another time, depending on API, dosage form and the likelihood of seeing that prescription again within its experimentally determined shelf life. Thus, the batching routine (2000) groups prescriptions for preparation to optimize workflow, final dosage form and formulation. Each batch (group of individual prescriptions) is automatically associated with a lot number and batch record that can integrate with existing pharmacy databases.

The pharmacy fulfillment and verification of non-sterile compounding process 900 includes compound formulation (3000). Formulations begin with selecting and/or generating appropriate formulation records for each batch. These records are stored for tracking, tracing and accountability, and are directly printed/used to prepare the compound according to instructions. First, a Master Formulation Record (MFR) is selected from a database that provides the template instructions for preparing a compound of a specific active ingredient, dosage form, and strength. If an MFR that matches all parameters does not exist, the program checks other sources (e.g., cloud, database, and so forth) for an MFR with the desired active ingredient and dosage form and generates an MFR that provides desired strength (in this case stock formula concentration). Once an MFR is selected, a Compounding Record (CR) for the batch is generated. The CR contains the recipe, instructions, batch data, etc, in a standard format.

The pharmacy fulfillment and verification of non-sterile compounding process 900 includes compound fabrication (4000). A compound is prepared according to the CR instructions by a compounding pharmacist, a compounding pharmacist technician, and/or a machine/robotic system. The compound is provided to a machine that prepares the final dosage form. The compound is introduced to the machine in a container/cartridge which may be fully formulated (all ingredients present and mixed) or partially formulated with additional raw ingredients (e.g., $H_2O$) added and mixed by machine. Personnel and/or resources can be reassigned as soon as the compound is provided to the machine. The machine takes batch and prescription data to compute motion sequence that creates precisely dosed final dosage forms. Prescription strength, quantity and active ingredient input into the machine by human or communicated electronically. Active ingredient and dosage form is used to compute formula characteristics such as viscosity. These computed characteristics, strength/dose and quantity are processed by a printing path routine or live production algorithm. In other embodiments, characteristics from prior machine measurements may be used. Ultimately, the result of this algorithm is a set of motion commands (and any other sensor/component instructions) for the machine to follow to prepare the final dosage forms. First, it computes optimal size and shape for easy swallowing (in the case of oral administration) and precise dosing. This size and shape forms the base desired geometry for each unit. The algorithm generates a point distribution to represent the unit. Then, it generates/computes a multidimensional vector print path of at least four dimensions that translates the geometry of the point distribution into motion. This path is used to coordinate printer motion. Each vector is communicated to its respective motor to coordinate motion along an axis. Together, motion by print head extrudes the compound and builds the unit layer-by-layer through motion in the X-Y-Z plane. Note that motors act in sync with each other. The machine makes the decision to do varying degrees of pathing and may print layer-by-layer or extrude in one single extrusion motion (rate and path instructions still computed and instructed) depending on dosage form, computed final geometry/shape, and formula characteristics. Some dosage forms such as suppositories require molds for production and dispensing so the system will ensure the correct mold is placed by human or machine into build area and then the motor instructions are computed to extrude directly into each cavity/mold. The machine may search a database for known mold configurations or use optical sensors or cameras to examine the mold and compute appropriate dimensions to create motor instructions.

The pharmacy fulfillment and verification of non-sterile compounding process 900 includes compound/prescription verification (5000). Data is automatically collected throughout preparation and stored with the appropriate batch by lot number and the appropriate prescription/patient record within the batch. The machine records data unit-by-unit (individual tablet/final dosage form). The print path algorithm self-calibrates using live collected data as the machine executes the print. For example, the machine computes expected error using data points including motor feedback, position error, and computed arc length. It compares the expected error to the actual error as measured by the final weight computer vision size and/or volume of the mid-tablet and/or finishing unit. The calibration routine can use the difference between expected and actual to calibrate parameters including motor factors and path algorithm constants to continually minimize error. The weight/size of every unit produced is stored. At the end of the print, weights converted to provide strength/dose are reviewed by a pharmacist to verify prescription for dispensing. Differences in actual dose and prescription dose outside a preset margin of error will automatically generate a system alert/notification and will be clearly demarcated in the pharmacist review data. Moreover, optical verification may be used.

The pharmacy fulfillment and verification of non-sterile compounding process 900 includes notification of final dosage (6000). The machine will alert when the run is complete. The run is complete when the final dosage form is ready for pharmacist check and packaging. The pharmacist will verify the prescription including the output actual dose data. The machine can optionally complete packaging and labeling such as unit-dose packaging (e.g., blister packaging) with label printed onto pack. When the final compound is removed from the machine, it will automatically run a cleaning cycle. Optionally, the machine will run a cycle depending on the next work orders and risk of cross-contamination. When possible, work orders may be ordered to reduce cleaning cycles, e.g., by lining up orders for the same drug on the same machine in sequence of increasing strength; order hazardous drugs closer to time of regular daily cleaning cycle. The cleaning cycle may simply check that cartridge was removed correctly and build surface cleared as for many drug/dosage forms this is sufficient to consider the system clean and ready for the next order. Certain drugs will always trigger the cleaning cycle (e.g., hazardous). Cleaning cycle length can be manually adjusted or electronically adjusted based on collected environmental data.

Licensed physicians are allowed to compound medications for patients. In some states, physician dispensing is allowed on-site (at physician's office). Process 900 is easily supported in this setting. In fact, the semi-automated process 900 makes integration of compounding into physician dispensing much easier than existing workflows.

Pharmacies or physician groups with multiple locations can network machines to communicate across locations to central prescription database. Machines are anonymously networked across all locations to connect to a cloud database and transmit and aggregate anonymized data from all machines. This provides unprecedented data about compounded products. Insights into volume of compounded prescription drugs by dose, quantity, dosage form and more will be possible.

Unique unit-level data and built-in process gates also support improved tracking/tracing of dispensed scheduled drugs.

The process 900 supports real time pharmacy fulfillment when completely automated. Customized prescriptions can be prepared on-demand as prescriptions are received by a pharmacy.

The above system supports one or more fully-automated semi-distributed compound fulfillment centers. More specifically, a clinic gathers patient information that can be quickly evaluated by a physician who then generates a compound prescription as treatment if medically appropriate. The compound prescription is electronically sent to an optimal pharmacy in network. An optimal pharmacy network may be determined by capacity (e.g., machine time available now to dispense/turn around quickly), shipping or delivery time/cost (e.g., reduce distance between pharmacy and patient), and so forth.

Electronic verification of the prescription occurs before processing for preparing/dispensing to prevent production of an incorrect prescription.

One step involves automatically selecting and introducing the correct drug/dosage form cartridge (with appropriate drug concentration to deliver the prescription strength/dose). This step ends when the correct drug/dosage form cartridge is provided to an appropriate machine for compounding the final dosage form.

Drug/Dosage Form-specific pre-filled containers (cartridges or pods) are robotically/mechanically found, selected and picked from inventory (e.g., using RFID-chips or digital scanning of bar codes) and inserted into the appropriate machine (e.g., by availability and capability). The Drug/Dosage form must match prescription. NDC Codes for reimbursements may also be checked/verified.

A dosage form-specific mix/base formula is found, selected and picked. This may be by selecting the appropriate "tank" off the shelf and mechanically/robotically inserting into the mixing device or selecting and initiating the cartridge preparation process by selecting the appropriate mixing machine dedicated to that dosage form (e.g., hooked up "permanently" to a tank/reservoir of that dosage form's inactive ingredient mix) or the mixing machine is connected to the different possible dosage form tanks and can programmatically use the tank desired.

In this process, the API must be measured and mixed into the dosage form's inactive ingredient blend/metric. In a fully automated implementation, drug powders are measured by the mixing machine. The correct drug may be selected from inventory as either a container of drug powder (which the machine will measure and add) or by using pre-measured standardized drug packets/pods (e.g., standardized by API mass or masses that when used in their entirety produce the concentration(s) needed to cover the drug's full dose range).

In the case of chewable or oral dissolving dosage forms such as chewable gummy gels, flavors may also be fully customized and added/measured in this step in a manner similar to the API pods/packets so as to allow many different possible individual customizations.

A first pass verification/QC on this cartridge can be done before insertion if mixed on-demand.

When the cartridge is provided to an auto compounding machine, it also receives the prescription order it must prepare and dispense. At the time of packaging/dispensing the pharmacist usually will sign off on the order.

The prescription can be bar coded or otherwise identified, where the pharmacist can review a queue of ready prescriptions and click a button to approve each in sequences (program can present customized set of things pharmacist should check per prescription and document their responses for compliance, e.g., for a compound of XX check the color and send it along to final packaging for delivery (or pickup by patient).

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A method comprising:
in a system having at least one processor communicatively coupled to a memory and at least one database, wherein the processor is configured to execute computer readable instructions stored in the memory to perform operations including:
receiving, by the processor, a prescription from the at least one database for a non-sterile compound from a health care provider in real time via a formulating component;
generating, by the processor, a work order via the formulating component;
providing the non-sterile compound in a container;
introducing the container and non-sterile compound therein to a fabrication component having a printer including a print head;
computing, by the processor, appropriate motor instructions for the print head of the fabrication component to extrude a correct amount of the non-sterile compound per a dosage based on active pharmaceutical ingredient (API)/formulation and strength, the computing step including: (i) retrieving the API/formulation and strength from the at least one database; (ii) computing a geometric size and shape of the non-sterile compound based on the retrieved API/formulation and strength; and (iii) generating a multi-dimensional vector print path based on the computed geometric size and shape of the non-sterile compound, the fabrication component capable of reading work orders received from the formulating component;
executing the computed instructions to produce final dosage forms to fulfill an order,
extruding the non-sterile compound from the print head using the generated multi-dimensional vector print path and producing the final dosage forms containing the non-sterile compound;
receiving final dosage forms from the fabrication component via a dispensing component; and
packaging and labeling the final dosage forms for dispensing to the patient.

2. The method of claim 1, further comprising the steps of:
identifying the non-sterile compound in the received prescription in real time;
batching the identified non-sterile compound in the received prescription for a compounding process;
formulating the identified non-sterile compound in the received prescription to yield a formula;

compounding the identified non-sterile compound in the received prescription from the formula; and filling the prescription for the non-sterile compound in real time.

3. The method of claim 2, wherein compounding comprises providing the formula to the formulating component that prepares the final dosage forms.

4. The method of claim 3 further comprising verifying the compounded non-sterile compound.

5. The method of claim 4 wherein verifying comprises automatically collecting data throughout compound preparation and storing the data by lot number and an appropriate prescription/patient record.

6. The method of claim 4 further comprising notifying a patient that the verified compound is ready for pickup.

7. The method of claim 2, wherein batching comprises cross-referencing available resources.

8. The method of claim 7 wherein available resources include one or more of compounding equipment, personnel, personnel training levels, inventory, API and inactive ingredients, tanks and pods.

9. The method of claim 2, wherein formulating comprises selecting or generating appropriate formulation records for a batch.

10. The method of claim 1, further comprising the step of extracting from the prescription one or more of dosage form, drug, strength, quantity, patient allergies, reason for compounding, urgency, patient address, delivery and pick-up request, the extracting step being performed by the formulating component.

11. The method of claim 1, further comprising the steps of generating and transmitting a secure message/request to prompt the health care provider for information for fields that are unclear, nonsensical or invalid, and/or to approve changes, the generating and transmitting steps being performed by the formulating component.

12. A method comprising:
in a system having at least one processor communicatively coupled to a memory and at least one database, wherein the processor is configured to execute computer readable instructions stored in the memory to perform operations including:
receiving, by the processor, a prescription from the at least one database for a non-sterile compound from a health care provider in real time;
identifying, by the processor, the non-sterile compound in the received prescription in real time;
batching, by the processor, the identified non-sterile compound in the received prescription for a compounding process;
formulating, by the processor, the identified non-sterile compound in the received prescription to yield a formula;
compounding, by the processor, the identified non-sterile compound in the received prescription from the formula;
providing the identified non-sterile compound in a container;
introducing the container and identified non-sterile compound therein to a fabrication component having a printer including a print head;
computing, by the processor, appropriate motor instructions for the print head of the fabrication component to extrude a correct amount of the non-sterile compound per a dosage based on active pharmaceutical ingredient (API)/formulation and strength, the computing step including: (i) retrieving the API/formulation and strength from the at least one database; (ii) computing a geometric size and shape of the non-sterile compound based on the retrieved API/formulation and strength; and (iii) generating a multi-dimensional vector print path based on the computed geometric size and shape of the non-sterile compound, the fabrication component capable of reading work orders received from the formulating component;
executing the computed instructions to produce final dosage forms to fulfill an order;
extruding the identified non-sterile compound from the print head using the generated multi-dimensional vector print path;
building a dosage form containing the identified non-sterile compound layer-by-layer through motion in the X-Y-Z plane; and
filling the prescription for the non-sterile compound in real time.

13. The method of claim 12, wherein the extruding step includes extruding the identified non-sterile compound directly into a mold.

14. The method of claim 13, further comprising using optical sensors or cameras to examine the mold and compute appropriate dimensions to create motor instructions therefor.

15. The method of claim 12, wherein compounding comprises providing the formula to the formulating component that prepares the final dosage forms.

16. The method of claim 12, further comprising verifying the compounded non-sterile compound.

17. The method of claim 16 wherein verifying comprises automatically collecting data throughout compound preparation and storing the data by lot number and an appropriate prescription/patient record.

18. The method of claim 12, wherein batching comprises cross-referencing available resources.

19. The method of claim 18 wherein available resources include one or more of compounding equipment, personnel, personnel training levels, inventory, API and inactive ingredients, tanks and pods.

20. The method of claim 12, wherein formulating comprises selecting or generating appropriate formulation records for a batch.

* * * * *